United States Patent [19]

Folden et al.

[11] Patent Number: 5,250,041
[45] Date of Patent: Oct. 5, 1993

[54] TUBING ADMINISTRATION SET FOR USE IN PERITONEAL DIALYSIS

[75] Inventors: Thomas I. Folden, Alamo, Calif.; Arnold Gross, Freisen, Fed. Rep. of Germany

[73] Assignee: Fresenius USA, Inc., Walnut Creek, Calif.

[21] Appl. No.: 821,090

[22] Filed: Jan. 16, 1992

Related U.S. Application Data

[63] Continuation-in-part of Ser. No. 07/621,421, Nov. 30, 1990, abandoned.

[51] Int. Cl.$^5$ .............................................. A61M 25/00
[52] U.S. Cl. ................................. 604/284; 604/905; 604/280; 604/29; 137/68.1
[58] Field of Search .............. 604/905, 280, 283, 284, 604/29, 49, 200, 244, 206, 82, 87, 89, 91, 335, 339; 137/68 R

[56] References Cited

U.S. PATENT DOCUMENTS

| | | | |
|---|---|---|---|
| 3,127,892 | 4/1964 | Bellamy et al. | 604/408 |
| 4,668,217 | 5/1987 | Isono | 604/29 |
| 4,778,447 | 10/1988 | Velde et al. | 604/29 |
| 4,810,241 | 3/1989 | Rogers | 604/29 |
| 4,878,516 | 11/1989 | Mathieu | 604/29 |
| 5,053,003 | 10/1991 | Dadson et al. | 604/29 |

*Primary Examiner*—C. Fred Rosenbaum
*Assistant Examiner*—C. Smith
*Attorney, Agent, or Firm*—Beaton & Swanson

[57] ABSTRACT

Apparatus for administering dialysis, including a separable tubing coupling (32). The tubing coupling (32) consists of a hollow cylindrical element (42, 44) insertable into the lumens of the distal and proximal regions of the fluid delivery tube (16), and has a scored circumference at which the coupling can be broken-off by application of an adequate bending force. The device allows rapid and reliable disconnecting of the patient from the dialysis apparatus, without the need for scissors or a knife to be employed.

3 Claims, 2 Drawing Sheets

TUBING ADMINISTRATION SET FOR USE IN PERITONEAL DIALYSIS

The present invention relates to improved means for performing manual and automatic peritoneal dialysis. More specifically, the invention is directed at an efficient and simple means for connecting and disconnecting the fluid delivery tube that runs from the dialysis solution to the peritoneal cavity of the patient. The invention includes a scored plastic coupling connecting proximal and distal segments of the delivery tube which can be broken along the scoring to disconnect the tube.

In the present state of the art, there are two commonly used techniques for the treatment of patients who have experienced significant renal failure. The traditional therapy has been haemodialysis, where the patient's blood is passed through filters that will remove the metabolic products from the patient's blood stream.

The second technique is peritoneal dialysis, where solutions are cycled into and out of the peritoneal cavity of the patient and wastes are removed with the spent solution.

Both techniques operate by the principles of diffusion across semipermeable membranes. In the case of peritoneal dialysis, the membrane that is used is the patient's peritoneal membrane. Although not as efficient as haemodialysis, peritoneal dialysis offers several advantages that have enhanced its desirability. For example, automated devices have been developed that allow a patient to undergo a dialysis treatment at night while the patient is asleep. Utilising these automated devices allows the patient greater mobility and more free time.

Peritoneal dialysis can be accomplished in several different modes. In CAPD (Continuous Ambulatory Peritoneal Dialysis), the infusion of solution into and out of the peritoneal cavity is accomplished while the patient functions normally throughout the day. The obvious disadvantages of CAPD are the cumbersome devices that must be worn by the patient. Examples of CAPD systems are disclosed in U.S. Pat. Nos. 4,747,822 of Peabody and 4,620,846 of Goldberg.

Two types of peritoneal dialysis therapies that are particularly suitable for use with automated systems are, on the one hand, the IPD-system (Intermittent Peritoneal Dialysis) and, on the other hand, the CCPD-system (Continuous Cycling Peritoneal Dialysis). In the IPD-system, large volumes of dialysis solution (up to 40 liters) are cycled through the patient's peritoneal cavity over a period of 4 to 24 hours. In the CCPD-system, the dialysis treatment is more or less continuous, with a treatment time of 3 to 4 hours at night and then, throughout the waking time of the patient a single charge of dialysis solution is retained during the day within the peritoneal cavity of the patient. There are certain advantages to each of these two different therapy techniques.

In both methods, not only IPD but also CCPD, an automated dialysis apparatus operates in generally the same manner. The dialysis solution and tubing administration set is integrated with the valving, heating and control functions associated with the automated apparatus. In many of the systems, pre-measured volumes of dialysis solution are either pumped or delivered by gravity flow to a heating station. At the heating station the solution is warmed to body temperature in order to prevent the uncomfortable sensation of introducing a solution at room-temperature or cooler into the peritoneal cavity. The warmed solution is then delivered from the dialysis station to the patient's peritoneal cavity via a fluid delivery tube which is essentially flexible tubing connected to the end of a catheter that enters the patient's peritoneal cavity. After a period of time (the "dwell period"), the solution is drained from the patient into a receiving container.

In the IPD-system, a large volume of solution is cycled in this manner during a relatively short period of time. Once treatment is completed, the patient is unencumbered for at least a few days. A disadvantage is the large volume of dialysis solution that must be utilised. Bags containing 40 liters of solution can be difficult to lift for a patient in a weakened condition.

With CCPD- and CAPD-methods, the same efficaceous results are obtained by increasing the dwell time of the dialysis solution within the peritoneal cavity. The total volume of solution can therefore be significantly reduced. The obvious disadvantage is that there is less "down time" for the patient to recover from the treatment.

The delivery tube in the PD-therapy generally includes a flexible tubing to transfer fluid to and from the catheter site, a catheter to enter the peritoneal cavity, and a connector between the tubing and the catheter. A detachable manual clamp is fitted onto the tubing to occlude the tubing as it is being connected to the catheter by means of the connector. Also included is a manually actuated permanent clamp to occlude the tubing permanently when the dialysis is completed so that the tubing can be disconnected from the catheter connector without spilling any of the fluid drained from the peritoneal cavity. A wide variety of PD-systems are known in the state of the art and are used in a number of different applications.

Upon completion of the CCPD, it is necessary to disconnect the patient from the tubing set. This is normally accomplished by occluding the delivery tube by closing the permanently attached manual clamp, and then cutting through the tubing on the side of the permanently manual clamp away from the patient. The permanent manual clamp thereby occludes the delivery tube on the patient side in order to prevent any spilling of the drained fluid. After the tubing is cut, a clamp on the catheter side is used to occlude the catheter. The stub of the tubing is removed from the catheter when the PD-system is next changed. A new PD-system is then connected to the catheter, the catheter clamp is opened and the process is repeated. The cutting of the delivery tube is normally accomplished with a pair of scissors or a knife. The PD-therapy is distinguished by the fact that it can be carried out by the patients themselves, without the help of a nurse or other person, and the scissors or knife must be located so that the patient can reach them while still connected to the tubing set.

Another drawback to a system in which the delivery tube is cut with a knife or scissors is that there is no indicator on the delivery tube as to where it should be cut. A frequent problem, therefore, is that the patient unfortunately cuts the delivery tube on the patient side of the clamp, thereby spilling drainage fluid. Even worse, the patient sometimes inadvertently cuts the catheter rather than the tubing, thereby requiring the removal of the damaged catheter and its replacement with a new catheter.

It is therefore the task of the present invention to solve the problem of the prior state of the art in such a manner that an accidental cutting of the delivery tube is prevented.

This problem is solved in accordance with the present invention by providing means in the region of the delivery tube so that said delivery tube can be separated from the remainder of the tubing.

The tubing of the delivery tube in accordance with the invention includes a plastic coupling toward the tubing end that goes to the catheter in the patient's peritoneal cavity. In accordance with a first embodiment, the coupling divides the tubing into a segment proximal to the peritoneal cavity and a segment distal to the peritoneal cavity, the two segments being connected by the coupling. The coupling is a hollow cylindrical element, one end of which is inserted into the open end of the distal tubing segment and the other end is inserted into the open end of the proximal tubing segment. The coupling is retained in the tubing by a friction fit or sealing-in with a solvent. An annular lip around the circumference of the coupling at or near its centre expediently serves as a stop for the ends of the tubing. The coupling is scored around its circumference near the annular lip.

When the PD-procedure is completed, and the delivery tube is suitably clamped, the coupling is easily broken at its nominal breaking-off site by strong bending. In this way, neither scissors nor knife is needed, so that there is no danger that the delivery tube will be cut through on the wrong side of the clamp or that the catheter itself will be inadvertently cut through.

In an additional advantageous further development of the invention, a Y-shaped connector piece is used for connection of the tubing. The first tube from the Y-piece goes to the patient, the second tube goes to a bag filled with fresh flushing solution and the third tube goes to a waste discharge tube. According to this second example of embodiment, the nominal breaking-off site is located around the outer circumference of the Y-branch which is connected to the first tube.

Further details, features and advantages will be dealt with in the following description of examples of embodiment, with reference to the accompanying drawings, in which.

Figure 1:
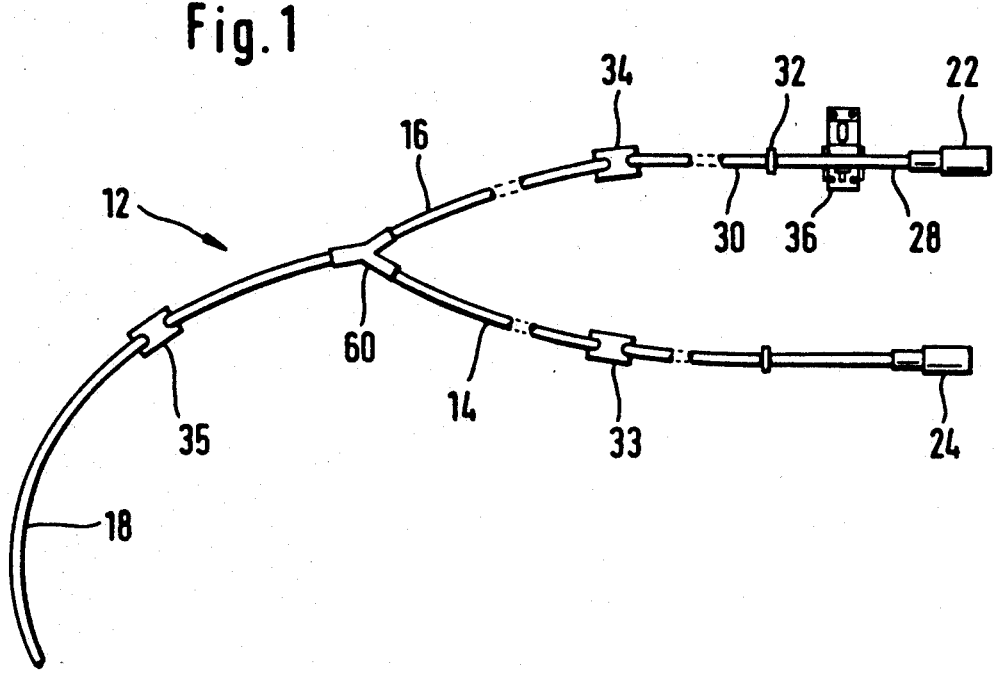
FIG. 1 is a view of a portion of a tubing set in accordance with the present invention, for use with an automated peritoneal dialysis apparatus.

FIG. 1 shows a region 12 of a tubing set for use with an automated peritoneal dialysis apparatus (not shown). The tubing set portion 12 includes a fluid supply tube 14, a fluid delivery tube 16 for connection to a peritoneal catheter, a drain tube 18 connected to a drain bag, and a Y-shaped connector for connecting the fluid supply tube 14, fluid delivery tube 16 and drain tube 18. At the end of the fluid delivery tube 16 is a connector 22 for connecting the fluid delivery tube to a peritoneal catheter. At the end of the fluid supply tube 14 is another connector 24 for connecting the fluid tube to a set (not depicted) of fluid containers.

The fluid delivery tube 16 includes a tube section 28 proximal to the patient's peritoneal cavity, a tube section 30 distal to the patient's peritoneal cavity and a tubing coupling 32 connecting the distal and proximal sections in the manner to be described further on. The fluid delivery tube 16 also includes a detachable manual clamp 34 on the distal tubing section 30 and a permanent manual clamp 36 on the proximal tubing section 28. The tubing is ordinary flexible plastic tubing for medical purposes. The detachable manual clamp 34 is an elongated open-ended pretensioned member with a pair of clamps on its inner surface that clamps onto the tube when the member is squeezed. An edge on one of the open ends snaps into a set of serrations on the other open end to hold the clamps onto the tubing, thereby partially or entirely occluding the tubing. The edge on one of the open ends can be disengaged from the serrations in the other open end by distorting the other open end away from the edge on the first open end. Clamps of this type are well known in the state of the art, and will not be further described here.

The permanent manual clamp 36 on the proximal tubing section 28 is also of a type that is well known in the state of the art. Briefly, it includes two hinged halves, the first of which can be slid on and snapped over the tubing and the second of which mates with the first by folding onto the first through the hinge. The second half has a protrusion which compresses and thereby completely occludes the tubing when it is folded over the first half. The first half includes a pair of hooks that snap into a pair of matching slots in the second half, thus permanently and entirely occluding the tubing.

Figure 2:
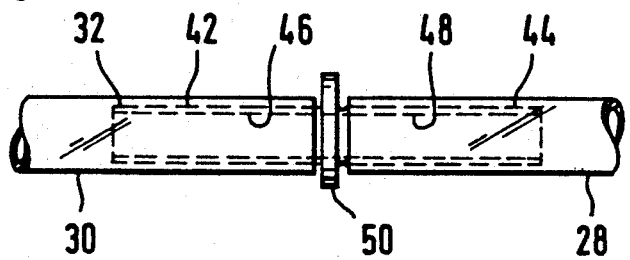
FIG. 2 is a separate view of the coupling, partly in section, shown attached to the delivery tube of the tubing set of FIG. 1.
Figure 3:
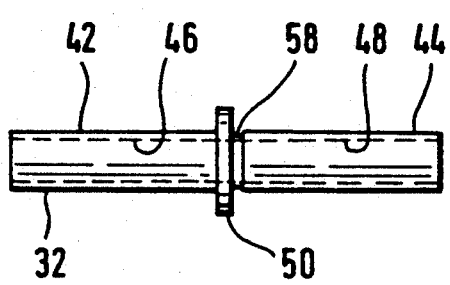
FIG. 3 is an separate view of the coupling in accordance with the present invention, shown detached from the tubing set

The tubing coupling 32 is better recognised in FIG. 2, where it is shown attached to the proximal tubing section 28 and the distal tubing section 30, and in FIG. 3 it is depicted detached from the tubing. The tubing coupling 32 includes a distal hollow cylinder 42 and a proximal hollow cylinder 44. Each of these cylinders is an elongated component with a central bore 46 and 48, respectively. The outside diameter of the hollow cylinders 42 and 44 tapers to a smaller diameter at each end. Preferably the maximum outside diameters are slightly greater than the inside diameter of the tubing into which they are inserted, so that the hollow cylinders can be pressed into the tubing to achieve a snug and watertight friction fit between the tubing coupling 32 and the tubing. The inside diameter of the hollow cylinders is as large as possible so that the fluid flow is not unduly restricted through the coupling, but not so large that the wall thickness of the hollow cylinders is so small that the tubing coupling 32 breaks under normal operating conditions. It has been found that, for use with polyvinyl chloride (PVC) medical-grade plastic tubing and a coupling formed from polycarbonate, these conditions can be met by having an inside diameter of 4 millimeters and a maximum outside diameter of 6.15 millimeters and a minimum outside diameter at both ends of 5.8 millimeters.

Positioned between the distal hollow cylinder 42 and the proximal hollow cylinder 44 of the tubing coupling 32, there is a raised annular stop 50 extending around the circumference of the hollow cylinders 42 and 44. The annular stop 50 acts as a detent for the distal tubing section 30 and proximal tubing section 28, so that each of them can be pushed onto the coupling to an appropriate extent to achieve a secure and watertight connection. In the preferred embodiment, each of the hollow cylinders 42 and 44 has a length of at least 25.4 millimeters and the annular stop has an outside diameter of 7.9 millimeters.

The proximal hollow cylinder 44 of the tubing coupling 32 is scored 58 around its outer circumference at a location adjacent to the raised annular stop 50, so that the coupling can be broken in the manner to be described further on. It has been found that, for a coupling wall thickness of 1 millimeter, a scoring depth of approximately 0.63 millimeter is sufficient to allow the coupling to be broken easily, without weakening the coupling to such an extent that it breaks accidentally. The scoring 58 may be on the distal hollow cylinder 42 rather than on the proximal hollow cylinder 44. In either position, the scoring 58 is preferably located adjacent to the raised annular stop 50, so that neither tube overlaps the breaking-off site appreciably and prevent the coupling from separating when it is broken.

Figure 4:
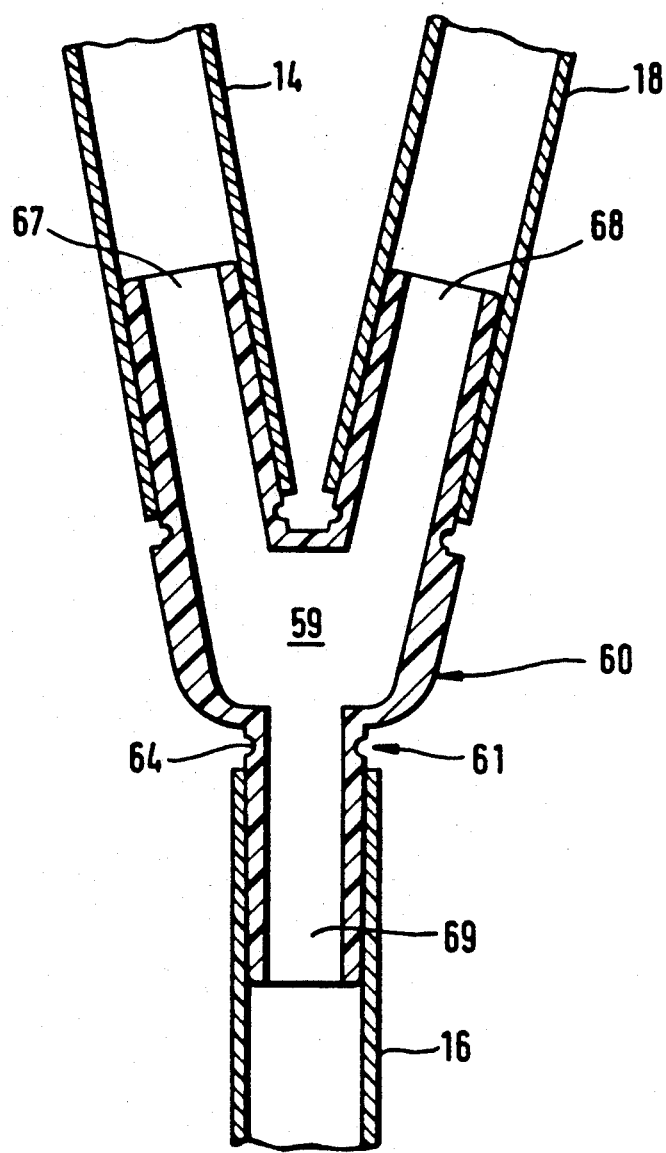
FIG. 4 is a section through the Y-shaped tube connector in accordance with the present invention showing the partly cut-away tubing.

In another advantageous form of embodiment of the invention, as depicted in FIG. 4, the means for separation is located in the region adjacent to the branching site 59 of the branch 69 of the Y-shaped tubing connector 60 which also possesses two other branches 67 and 68. The branches 67–69 are, as may be seen from FIG. 4, are connected to the tubing pieces 14, 18 and 16 respectively. In this arrangement, the nominal breaking-off site is indicated at 61. Said breaking-off site 61, similarly to the tubing coupling 32, possesses a scoring 64 which can extend around the entire circumference of the Y-branch 69. Because of the separating means on branch 69 of the Y-shaped tube connector 60, the tubing portion 16 to be broken-off can be readily and reliably separated from the Y-shaped tube connector 60.

As already indicated previously, the tubing coupling and the Y-shaped tube connector 32 may be made from a synthetic plastics material, in particular polycarbonate, and may be fabricated by injection moulding. Other materials and fabrication methods will be apparent to persons skilled in the art.

In operation, the tubing set 12 is positioned so that the fluid tube 14 is connected to one or more fluid containers (not depicted) which contain a solution suitable for the PD-procedure. The drain container 20 is suitably located at a position generally lower than the patient's peritoneal cavity. The fluid delivery tube 16 is connected to the catheter entering the patient's peritoneal cavity. The manual releasing clamps 34 and 33 on the fluid delivery tube 16 and on the fluid tube 14 respectively are opened, the manual releasing clamp 35 on the drain tube 18 is released so that the spent fluid is usually discharged under the influence of gravity. The clamp 35 is then closed and the clamp 34 on the fluid delivery tube 16 is opened so that fresh PD-fluid from the fluid container bags (not depicted) can flow through the fluid tube 14 and the fluid delivery tube 16 into the peritoneal cavity. Following this the manual releasing clamp 34 and the permanent manual clamp 36 are closed to occlude the fluid delivery tube 16 completely. The fluid delivery tube 16 is then separated into the proximal section 28 and distal section 30 by breaking the tubing coupling 32 in accordance with the first form of embodiment. The breaking of the tubing coupling 32 is accomplished by grasping each end and bending it so that it breaks cleanly along the scoring 38. The proximal tubing section 28 can be removed from the catheter when the system is being changed over.

In accordance with another form of embodiment, the Y-shaped piece is grasped on the one side by the two branches 67 and 68 and on the other side by the branch 69 and then bent in such a way that it breaks off at the nominal breaking-off site, thus freeing the branch 69. Because of this separating operation of the fluid delivery tube 16 by the breaking of the tubing coupling 32 or of the Y-shaped piece, the effect is achieved that there is no need for either a knife or for scissors or for any other tool at all to effect this separating operation.

Moreover, this tubing arrangement 12 for separating the fluid delivery tube 16 ensures that the separation will occur at the tubing coupling 32 or at the Y-shaped piece 60 rather than on the wrong side of the clamp or some other incorrect location, since the permanent manual clamp 36 is installed in the position on the working side between the nominal breaking-off site 58 or 64 and the connector 22 on the patient side. In conclusion, it can be stated that this results in a simple, inexpensive and very safe and reliable system. Although the tubing coupling 32 and the Y-shaped tubing connector are described in relation to peritoneal dialysis, it will be apparent that the tubing coupling 32 may be used for other types of dialysis and for other medical and non-medical applications.

What is claimed is:

1. A peritoneal dialysis tubing administration set for use in administering fluid from a fluid container into a patient's peritoneal cavity through a peritoneal catheter and for discharging the spent fluid from the peritoneal cavity into a waste container, comprising: a tube connector; a fluid supply tube which at one end is in flow communication with the fluid container and at the other end with the tube connector; a fluid delivery tube which at one end is in fluid communication with the peritoneal catheter and at the other end with the tube connector, the fluid delivery tube including two segments; a waste discharge tube which is in flow communication at one end with the tube connector and at the other end with the waste container whereby there is fluid communication among all three of the tubes through the tube connector; clamps which could be used to occlude these tubes including a fluid delivery tube clamp, a fluid supply tube clamp and a discharge tube clamp; and a breakable tubing coupling having a first end inserted into one of said segments and a second end inserted into the other of said segments, said ends being able to be separated by breaking the tubing coupling, wherein the first end of the tubing coupling is a hollow cylinder in flow communication with said one of said segments and the second end of the tubing coupling is also a hollow cylinder in flow communication with said other of said segments, and the two hollow cylinders are in fluid communication with one another, where the hollow cylinders have an outside diameter greater than the inside diameter of the tube with which they are in flow communication, and where the hollow cylinders can be inserted into the tube to establish a water-tight connection, and wherein one of the hollow cylinders is circumferentially scored so that it could be broken to separate said segments.

2. A peritoneal dialysis tubing administration set for use in administering fluid from a fluid container into a patient's peritoneal cavity through a peritoneal catheter and for discharging the spent fluid from the peritoneal cavity into a waste container, comprising a tube connector; a fluid supply tube which at one end is in flow communication with the fluid container and at the other end with the tube connector; a fluid delivery tube which at one end is in flow communication with the peritoneal catheter and at the other end with the tube connector; a waste discharge tube which is in flow communication at one end with the tube connector and at the other end with the waste container whereby there is fluid communication among all three of the tubes through the tube connector, and the tube connector includes a branch connected to the fluid delivery tube, a branch connected to the fluid supply tube, and a branch connected to the discharge tube; clamps which can be used to occlude these tubes including a fluid delivery tube clamp, a fluid supply tube clamp and a discharge tube clamp; and separating means to separate the fluid delivery tube from the tube connector including scoring on the outer surface of the branch connected to the fluid delivery tube, by which the branch can be broken off along the scoring by application of a bending force.

3. The tubing administration set according to claim 2, wherein branch connected to the fluid delivery tube includes a stop means for halting the insertion of the branch into the fluid delivery tube at a predetermined insertion distance.

* * * * *